(12) United States Patent
Bruestle et al.

(10) Patent No.: US 9,539,667 B2
(45) Date of Patent: Jan. 10, 2017

(54) SYSTEMS AND METHODS FOR CONNECTION TO A TRANSDUCER IN ULTRASOUND PROBES

(71) Applicant: General Electric Company, Schenectady, NY (US)

(72) Inventors: Reinhold Bruestle, Zipf (AT); Thomas Rittenschober, Zipf (AT); Manuel Schoenauer, Zipf (AT)

(73) Assignee: General Electric Company, Schenectady, NY (US)

( * ) Notice: Subject to any disclaimer, the term of this patent is extended or adjusted under 35 U.S.C. 154(b) by 278 days.

(21) Appl. No.: 14/143,630

(22) Filed: Dec. 30, 2013

(65) Prior Publication Data

US 2015/0182194 A1    Jul. 2, 2015

(51) Int. Cl.
| | |
|---|---|
| *A61B 8/14* | (2006.01) |
| *B23K 26/36* | (2014.01) |
| *B06B 1/06* | (2006.01) |
| *G01S 15/89* | (2006.01) |
| *G01S 7/52* | (2006.01) |
| *A61B 8/00* | (2006.01) |

(52) U.S. Cl.
CPC ............ *B23K 26/365* (2013.01); *B06B 1/0622* (2013.01); *G01S 7/52079* (2013.01); *G01S 7/52082* (2013.01); *G01S 7/52084* (2013.01); *G01S 15/894* (2013.01); *G01S 15/8915* (2013.01); *A61B 8/4444* (2013.01); *A61B 8/4466* (2013.01); *G01S 15/8993* (2013.01)

(58) Field of Classification Search
CPC ... A61B 8/4444; A61B 8/4466; B06B 1/0622; B23K 26/362; B23K 26/365; G01S 15/8915; G01S 15/894; G01S 15/8993; G01S 7/52079; G01S 7/52082; G01S 7/52084

See application file for complete search history.

(56) References Cited

U.S. PATENT DOCUMENTS

| | | |
|---|---|---|
| 2007/0016056 A1 | 1/2007 | Kerwin |
| 2009/0299178 A1 | 12/2009 | Kim et al. |
| 2012/0238876 A1 | 9/2012 | Tanabe et al. |
| 2013/0172756 A1 | 7/2013 | Bruestle et al. |
| 2013/0253327 A1 | 9/2013 | Ko et al. |
| 2013/0315035 A1 | 11/2013 | Tai |

FOREIGN PATENT DOCUMENTS

KR    20130078207 A    7/2013

OTHER PUBLICATIONS

Invitation to Pay Additional Fees And, Where Applicable, Protest Fee (Form PCT/ISA/206) for PCT/US2014/049719, mail date Dec. 16, 2014, 8 pages.

(Continued)

*Primary Examiner* — Mark Remaly
(74) *Attorney, Agent, or Firm* — Dean D. Small; The Small Patent Law Group, LLC.

(57) ABSTRACT

Methods and systems for connection to a transducer in ultrasound probes are provided. One system includes transducer having a base configured to support thereon an ultrasound transducer array and a plurality of electrical interconnects integrated with the base. The electrical interconnects are configured to connect to the ultrasound transducer array and extend along at least a portion of the base from the ultrasound transducer array.

14 Claims, 8 Drawing Sheets

(56) References Cited

OTHER PUBLICATIONS

Soeren Hirsch et al., A new device with PZT ultrasonic transducers in MEMS technology, Journal of Physics: Conference Series, Institute of Physics Publishing, vol. 34, No. 1, Apr. 1, 2006, 6 pages.
International Search Report and Written Opinion regarding International Application No. PCT/US2014/049719, mail date Mar. 26, 2015, 18 pages.

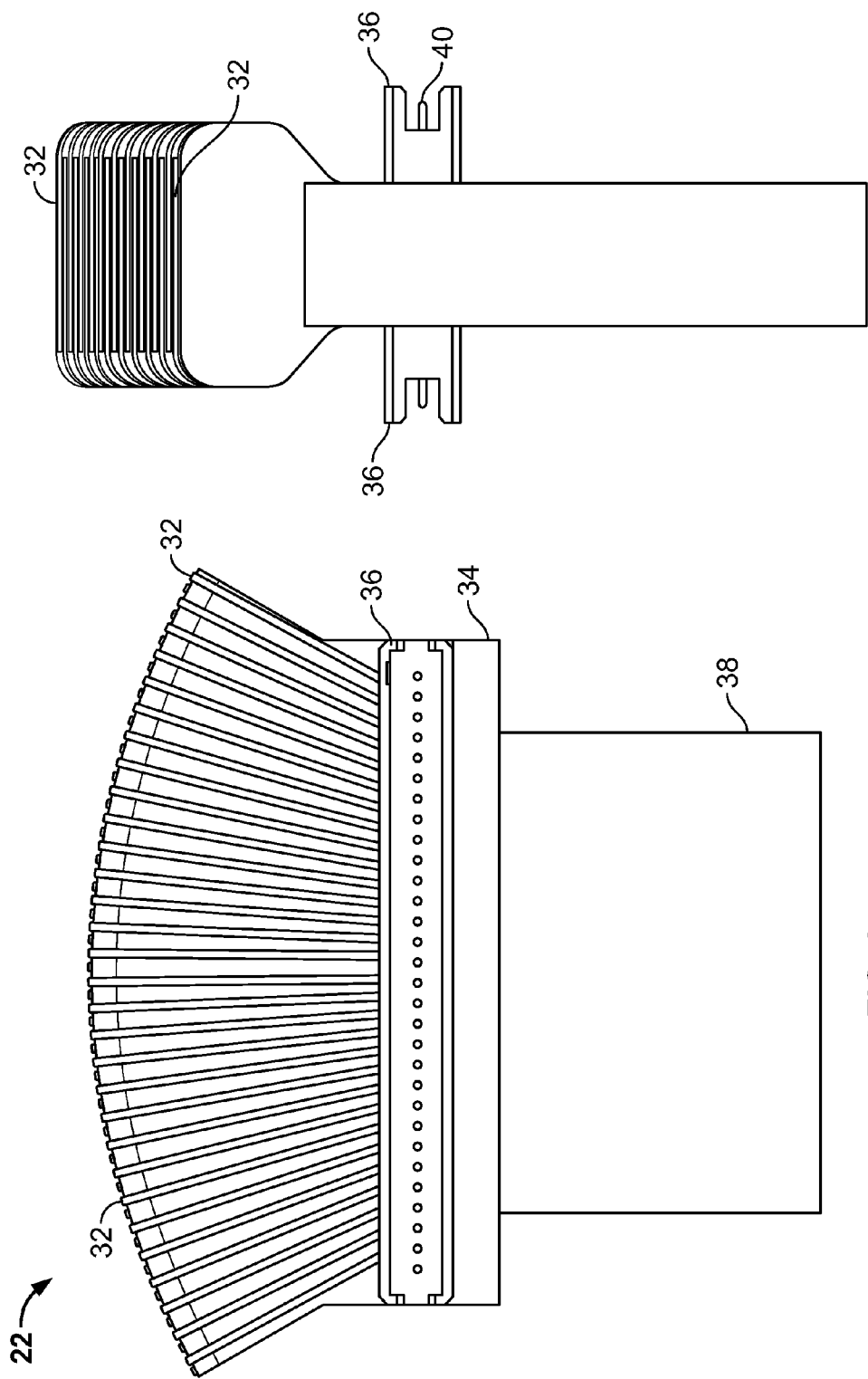

SYSTEMS AND METHODS FOR CONNECTION TO A TRANSDUCER IN ULTRASOUND PROBES

BACKGROUND OF THE INVENTION

Ultrasound systems typically include ultrasound scanning devices, such as ultrasound probes having one or more transducers that allow for performing various different ultrasound scans (e.g., different imaging of a volume or body). The ultrasound probes are typically connected to an ultrasound system that controls the operation of the probes. The probes include a scan head having a plurality of transducer elements (e.g., piezoelectric crystals), which may be arranged in an array. The ultrasound system drives the transducer elements within the array during operation, such as, during a scan of a volume or body, which may be controlled based upon the type of scan to be performed.

In some conventional probe configurations, the connection arrangement to the transducer array includes a number of different parts. For example, at least a structural part (carrier element) and an electrical interconnect (such a separate flexible connector) are used to connect to the transducer array. The flexible connector may include separate interconnections that are used to connect to the individual transducer elements. Additional elements also may be needed, such as board to board connectors to interface the transducer and various components within the probe, as well as to a system cable.

Thus, the transducer connection and scan head connection in conventional arrangements requires additional interconnects and parts. Accordingly, the assembly process can be more complex and the overall cost higher.

BRIEF DESCRIPTION OF THE INVENTION

In one embodiment, a transducer support for an ultrasound probe is provided. The transducer support includes a base configured to support thereon an ultrasound transducer array and a plurality of electrical interconnects integrated with the base. The electrical interconnects are configured to connect to the ultrasound transducer array and extend along at least a portion of the base from the ultrasound transducer array.

In another embodiment, an ultrasound probe is provided that includes a housing and a scan head within the housing, wherein the scan head has a transducer array supported on a molded interconnect device (MID). The MID includes integrated electrical interconnects electrically connected to the transducer array. The ultrasound probe also includes at least one processing or control board within the housing, wherein the processing or control board is electrically connected to the transducer array via the electrical interconnects of the MID.

In a further embodiment, a method for manufacturing a connection member for an ultrasound probe is provided. The method includes providing a base member formed from a thermoplastic having a heat activated metal complex. The method also includes forming electrical interconnects in the base member by etching traces into the base member using a heat source, wherein the electrical interconnects are formed within the thermoplastic to form a molded interconnect device (MID). The electrical interconnects are configured to electrically couple to a transducer array.

BRIEF DESCRIPTION OF THE DRAWINGS

FIG. 2 is a side view of a portion of the ultrasound probe in FIG. 1.

FIG. 3 is another side view of a portion of the ultrasound probe in FIG. 1.

DETAILED DESCRIPTION

Figure 1:
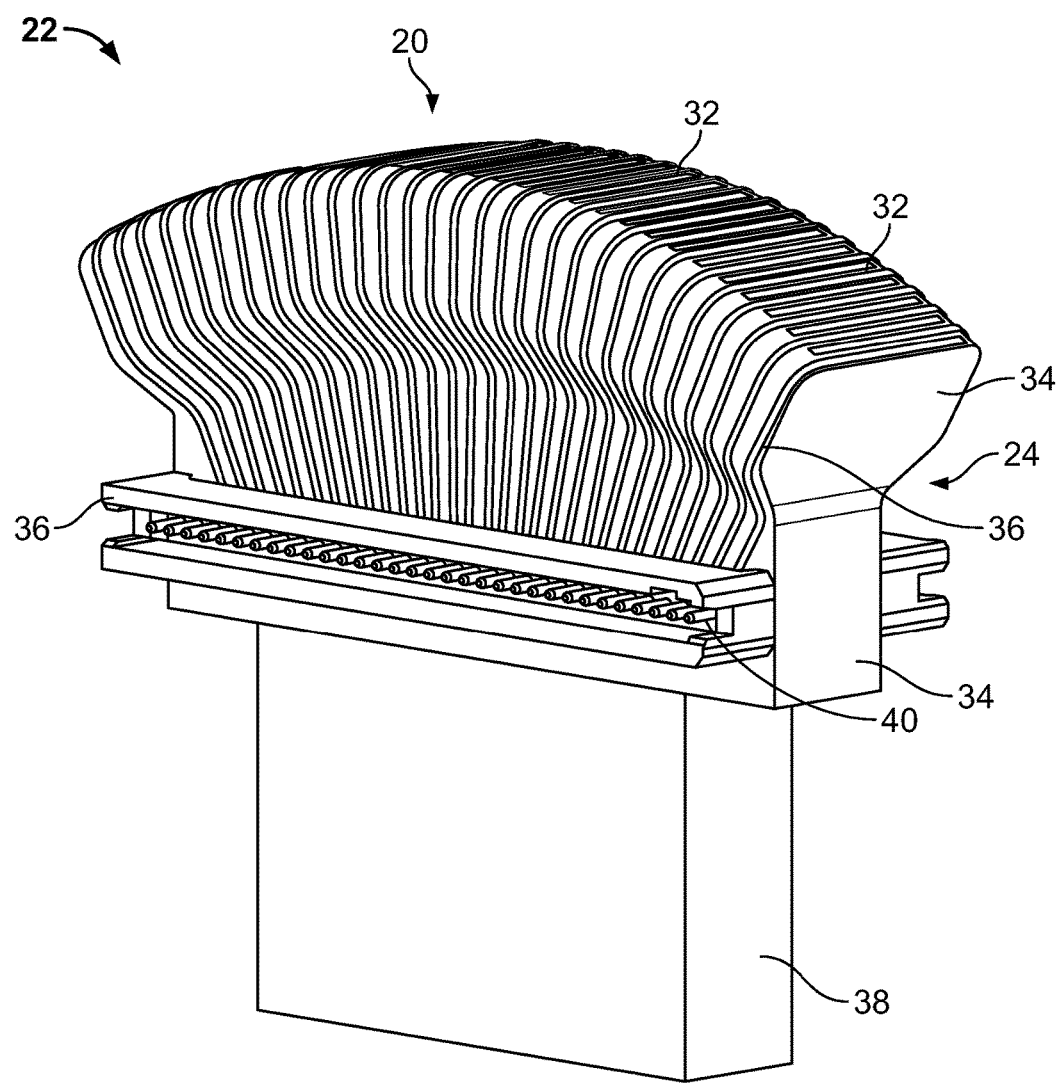
FIG. 1 is a perspective view of a portion of an ultrasound probe illustrating a transducer support in accordance with an embodiment having the probe housing removed.
Figure 4:
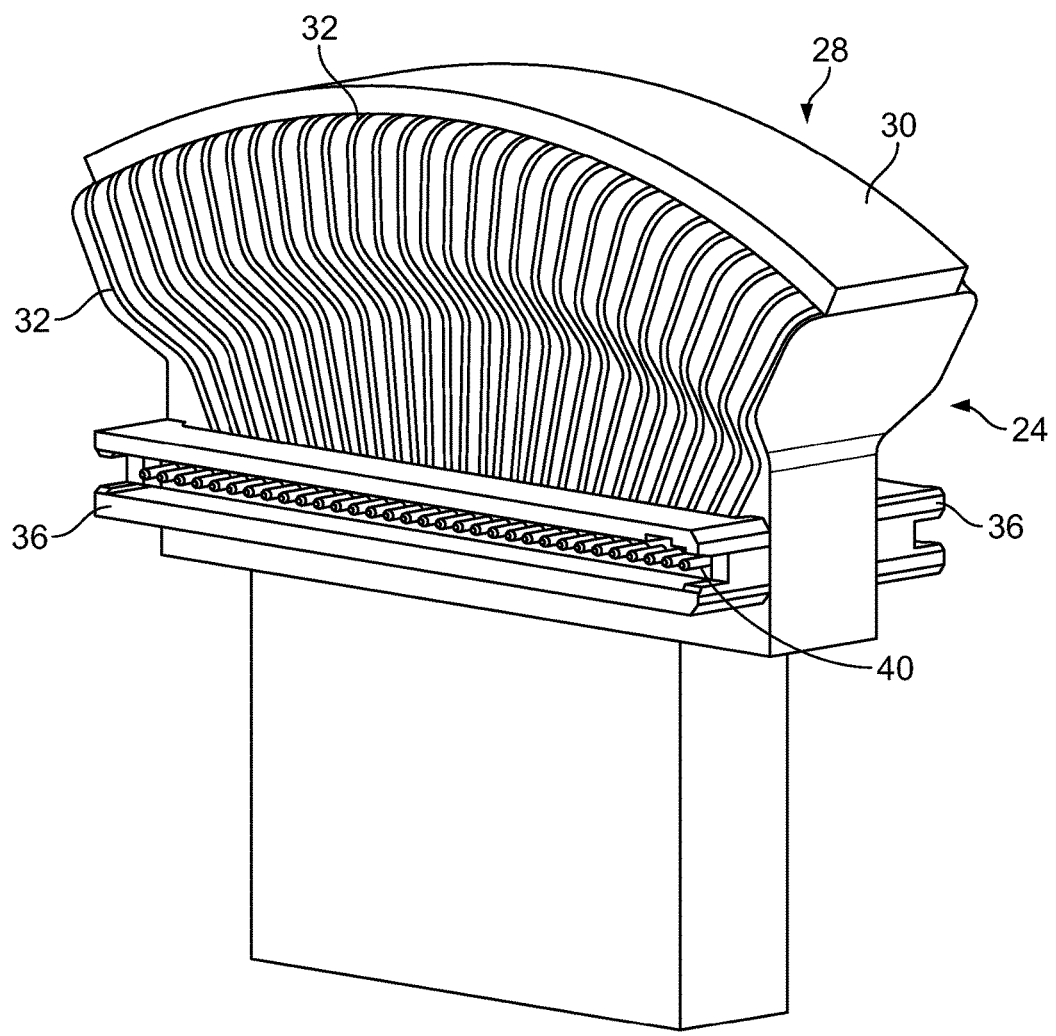
FIG. 4 is another perspective view of a portion of the ultrasound probe in FIG. 1.

The following detailed description of various embodiments will be better understood when read in conjunction with the appended drawings. To the extent that the figures illustrate diagrams of structural or functional blocks of the various embodiments, the blocks are not necessarily indicative of the division between hardware or circuitry. Thus, for example, one or more of the blocks may be implemented in a single piece of hardware or multiple pieces of hardware. It should be understood that the various embodiments are not limited to the arrangements and instrumentality shown in the drawings.

Described herein are various embodiments that provide a transducer support and interconnection arrangement for an ultrasound probe wherein a single integrated part or piece is provided for both the electrical interconnect portion and support portion for connecting to a transducer array of an ultrasound probe. By practicing one or more embodiments a simplified structure, higher robustness, and/or simpler assembly process may be provided. For example, a probe provided in accordance with some embodiments may have a reduced number of parts that are less expensive to produce and easier to assemble or replace within the probe.

More particularly, various embodiments provide a molded interconnect device (MID) for connection to a transducer array within an ultrasound probe. The MID in some embodiments is an injection-molded thermoplastic part or piece with integrated electronic circuit traces, which may be used, for example, to connect the transducer array elements to an interface or system cable. For example, high temperature thermoplastics and structured metallization may be used for a circuit carrier design within the ultrasound probe. In various embodiments, a plastic substrate/housing may be combined with circuitry into a signal part using selective metallization. In one embodiment, the structural part (e.g., carrier) is integrated with the electronic interconnect (e.g., transducer interconnects) into one integrated part. Thus, in some embodiments, the various components such as the carrier and transducer flex connection are combined and integrated into a single piece, which may be a single unitary design in some embodiments. For example, in an ultrasound probe having a dematching layer type of transducer, the carrier block may be formed from plastic and provide an acoustic design performance for different applications. In various embodiments, a three-dimensional (3D)-MID is provided that allows a construction or configuration having a plastic carrier part with structurized metal traces applied or formed thereon or therein to interconnect to the acoustic stack that may be laminated on top of the plastic carrier. In some embodiments, a connector or interface (e.g., a board-to-board connector) to interface the transducer to, for example, a cable can be directly populated on the plastic carrier. For example, the connector or interface may be coupled to a plastic base using different fastening or coupling arrangements, which may include, solder or epoxy.

It should be appreciated that although the MID is described for connection to transducer array elements and communicating signals to and from the transducer array elements, one or more embodiments, including the MID, may be used for different types of connections within the ultrasound probe, at different portions of the ultrasound probe, and to communicate different types of signals, power, etc. It also should be noted that although the various embodiments are described in connection with a probe having a particular mechanical configuration, the connection arrangement of the various embodiments may be provided in different types and configurations of probes.

In particular, various embodiments provide an ultrasound probe 20, a portion of which, namely a scanning end 22, having an integrated support and electrical connection member illustrated as an MID 24 in accordance with an embodiment, is shown in FIGS. 1-4. It should be noted that although the embodiment illustrated in FIG. 1 is a scanning end 22 for a non-mechanically moving probe, various embodiments may be implemented in a mechanically moving probe design wherein the scanning end 22 mechanically moves within the probe housing. For example, the ultrasound probe may be an ultrasound imaging probe having a non-mechanically moving (e.g., electronically steerable) or mechanically moving scan head, which includes a transducer carrier (provided by the MID 24) for supporting a transducer array 28 (which in various embodiments may be formed from piezoelectric ceramic elements and a dematching layer or acoustic stack laminated thereon). However, it should be noted that various embodiments may be implemented in different types of probes having different designs and are not limited to the probes illustrated and described herein.

The transducer array 28 in various embodiments may be formed from any suitable components, for example, a piezoelectric ceramic 30 and a backing strip (or backing layer, such as a dematching layer, not shown) which is supported on the MID 24, which in the illustrated embodiment is the carrier member and also includes the electrical interconnects (e.g., electrical traces) integrated therewith as described in more detail herein. It should be noted that although the transducer array 28 is shown as a curved array element, different configurations may be provided. For example, the transducer array 26 may be a linear array.

In various embodiments, arrangements for communicating with and electrically controlling the transducer array 28 are also provided as described in more detail herein, which generally includes electrical interconnects 32 (e.g., electrical traces) integrated with the MID 24 to define a single support and interconnect member. For example, as shown in the illustrated embodiments, the electrical interconnects 32 are applied to or formed on a base 34, such as a plastic base member as described in more detail herein (e.g., along a top surface of the base 34 and also along at least a portion of one side of the base 34). Thus, in various embodiments, a single interface and support element, such as the MID 24, is provided having the electrical interconnects and support portion for the transducer array 28 combined or integrated into a single physical structure or part. In some embodiments, the MID 24 provides the functionality and/or operation of a support structure and electrical interconnect (instead of, for example, a separate carrier and scan head flex PCB). The MID 24 in various embodiments supports and provides interconnection to the transducer array 28 within the probe.

In this illustrated embodiment, a pair of connectors 36 are also coupled to the MID 24 to allow connection to the electrical interconnects 32, such as for connection to a system cable. It should be noted that although two connectors 36 are shown, fewer or additional connectors 36 may be provided and coupled to the same or different portions of the MID 24, such as based on the configuration of the probe. The connectors 36 may be any suitable type of connection interface, which in one embodiment is a board-to-board connector, such as for cable interconnect and includes a plurality of connector elements 43 (illustrated as connector pins). For example, the connector elements 43 may be configured to connect to complementary connectors of a coaxial connector for a 2D probe. However, it should be appreciated that the connector 36 may be configured to connect to different types of cables or interconnects.

In the illustrated embodiment, an additional portion 38 may be provided that extends from the base 34, which may be coupled thereto or form part of the base 34. In various embodiments, the portion 38 allows for connection of the MID 24 in the probe, such as mounting of the MID 24 to and within the housing of the probe.

Figure 5:
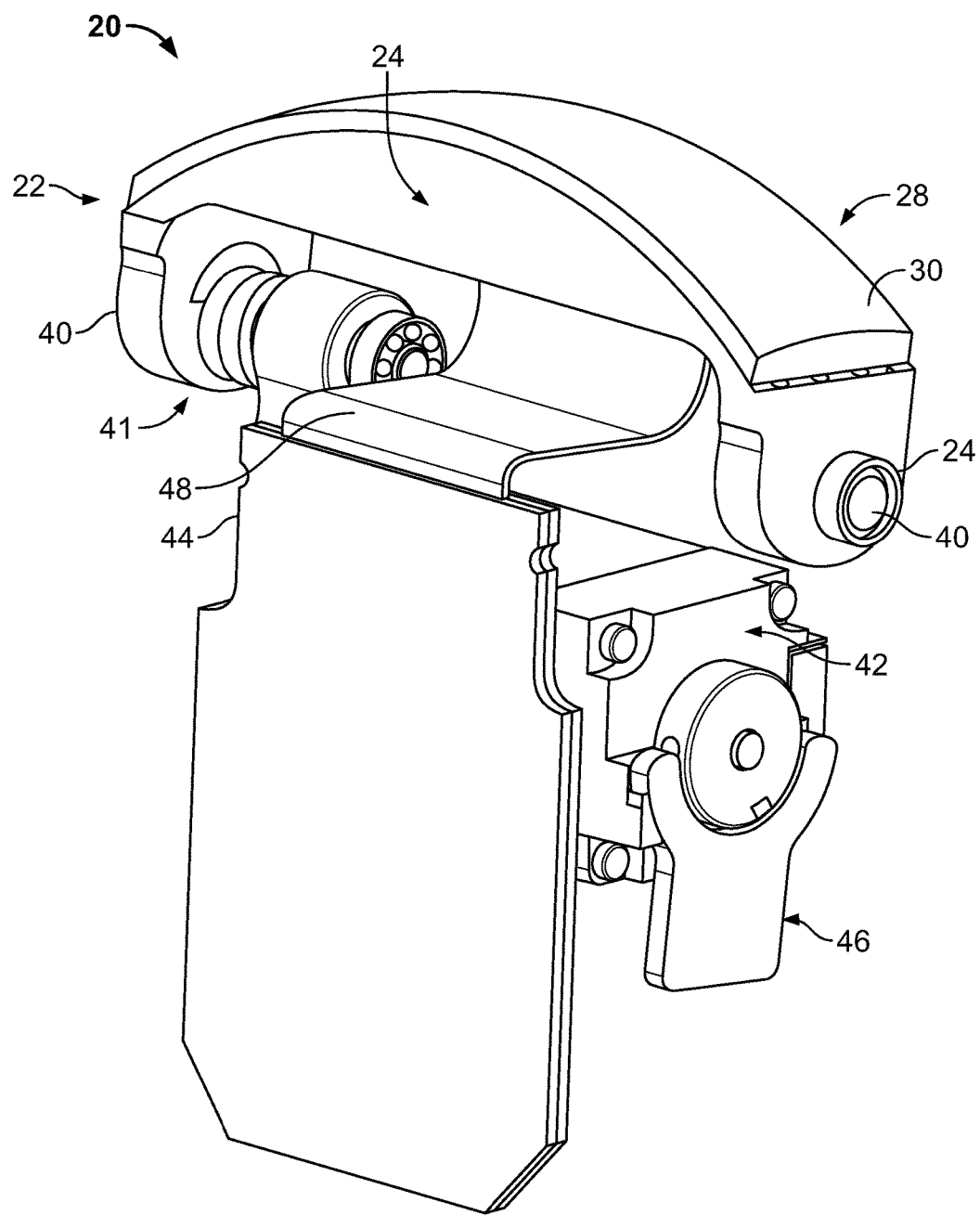
FIG. 5 is a perspective view of a portion of an ultrasound probe in accordance with another embodiment illustrating a transducer support.

In one embodiment, the scan head 22 may be in a chamber (having an acoustic liquid therein in some embodiments) and may include a transducer driving arrangement for moving (e.g., rotating) the transducer array 28 (in the embodiment of FIG. 5) and a transducer control arrangement for selectively driving elements of the transducer array 28 (e.g., the piezoelectric ceramic 30 of the transducer array 28). For example, in a mechanically moving probe as shown in FIG. 5, the transducer driving arrangement may include a transducer axle 40 in connection with the scan head 22, for example, coupled to the scan head 22 and extending within a drive shaft opening formed within the scan head 22. It should be noted that the MID 24 in various embodiments defines a connector and support member within the scan head 22 for supporting the transducer array 28 and providing electrical interconnect thereto.

In this embodiments, the MID 24 defines a transducer carrier such that when the transducer axle 40 moves, in particular rotates, to move the scan head, movement of the transducer array 28 mounted thereto is also provided. It should be noted that the electrical interconnects 32 (shown in FIGS. 1-4) are coupled to the transducer array 28 such that the connector 36 (shown in FIGS. 1-4) is electrically connected to the transducer array 28.

It also should be noted that different configurations may be provided. For example, although the scan head 24 as shown in FIG. 5 may be mounted to two separate transducer axles 40 that do not extend entirely between the side walls of the scan head, different sizes of transducer axles may be provided. Additionally, in some embodiments, a single transducer axle 40 may be provided. In the illustrated embodiment, the transducer axle 40 engages a gear arrangement 41, which in this embodiment is a toothed gear arrangement coupled to a motor 42. However, other arrangements to drive the transducer axle 40 may be provided, for example, a ball drive arrangement or a two-stage gear arrangement having a belt drive and a rope drive. Additionally, ball bearings may be provided in connection with the transducer axle 40, which reduces rotational friction and supports radial and axial loads. It should be noted that the lengths and dimensions of the various embodiments may be varied as desired or needed.

The transducer array 28 is in connection with one or more processing or control boards 44 via the connectors 36 (using a cable 48) that provide communication therebetween. For example, the one or more processing or control boards 44 may be tuning and/or termination boards for the transducer array 28, which may be formed from rigid PCBs. However, any other type of processing or control board may be provided as desired or needed. Other components also may be provided in some embodiments. For example, in one embodiment, an alignment sensor 46 may be provided, which may be a Hall sensor PCB that operates to provide center position alignment of the transducer array 28.

Thus, various embodiments include the MID 24 that provides support and electrical connection to the transducer array 28. The transducer array 28 may be coupled to the MID 24 in different ways, including as known in the art. In some embodiments, the transducer array 28 may be coupled to the MID 24, such as to the top surface of the MID 24 using an epoxy or thin bonding. The coupling of the transducer array 28 to the MID 24 electrically connects the elements of the transducer array 28 to the electrical interconnects 32 provided as part of the MID 24. For example, in some embodiments, a gold to gold interconnect may be provided with the assembly then laminated, such as using a high temperature or pressure (e.g., a suitable temperature as known in the art to bond the interface between the elements).

The connectors 36 are also coupled to the MID 24. For example, the connectors 36 may be coupled to the MID 24 at a lower end of the base 34 to extend therefrom. In some embodiments, the connectors 36 are electrically coupled to the electrical interconnects 32 at one or more ends of the electrical interconnects 32 with the transducer array 28 coupled between the ends. Although the connectors 36 are shown extending generally perpendicular to the side surface of the base 34, the connectors 36 may be provided in different configurations and arrangements to extend at angles to or along the base 34 to allow connection thereto at different angles or along the base 34. The connectors 36 may be formed from a plastic material or other suitable material, such as a liquid crystal polymer, and soldered to the base 34 to electrically connect to the electrical interconnects 36. Thus, in various embodiments, a PCB or similar connector interface is not needed.

With respect to the MID 24, the base 34 with the electrical interconnects 32 may be formed using different processes, which in one embodiment, includes an injection-molded thermoplastic part or piece with laser scribing. However, other methods or processes may be used, such as, but not limited to, co-molding, backfill molding and electric flux methods, among others. For example, in some embodiments, a laser direct structuring (LDS) method may be used such that a thermoplastic material is doped with a metal-plastic additive activated by a laser or heat source. Accordingly, a single component that is injection molded is provided that allows for a laser to define the paths for the circuit traces to be formed on the plastic of the base 34, which may be later applied by different metallization processes. Other methods include, for example, two-shot molding with subsequent plating.

It also should be noted that various embodiments may be implemented in connection with transducers having specialized backing. It should be appreciated that the application or forming of the electrical interconnects 32 on the base 34 may be performed by different methods and processes, such as based on the particular application. Thus, in various embodiments, for example, the MID 24 is an injection-molded thermoplastic part with integrated electronic circuit traces, wherein the base 34 is formed from a high temperature thermoplastic. It should be noted that electrical isolation or insulation may be provided between adjacent electrical interconnects 32 or between pairs of electrical interconnects 32, for example, such that in some embodiments signal pairs of even and odd signals may be provided. It should also be noted that a coating or paint may be provided over the visible portions of the electrical interconnects 32 in some embodiments.

Thus, in various embodiments, the MID 24 may merge or combine multiple functions or functionality otherwise accomplished using different components. For example, in some embodiments, the MID 24 merges the functionality of a flex interconnect and transducer backing into a single piece. In some embodiments, the MID 24 provides a single integrated configuration for connecting the transducer array 28 from the scan head 24 to other portions within the probe (e.g., the processing or control boards 44) as well as supporting the transducer array 28 within the scan head 24.

In the illustrated embodiment, the top surface of the MID 24 has a length (L) and width (W) that is complementary to the transducer array 28. For example, in various embodiments, the top surface of the MID 24 is sized and shaped to allow for connection with and support of the transducer array 28. In one embodiment, the dimensions and shape of the MID 24 are provided (e.g., molded) such that transducer array 28 is coupled directly to the top surface of the MID 24.

Figure 6:
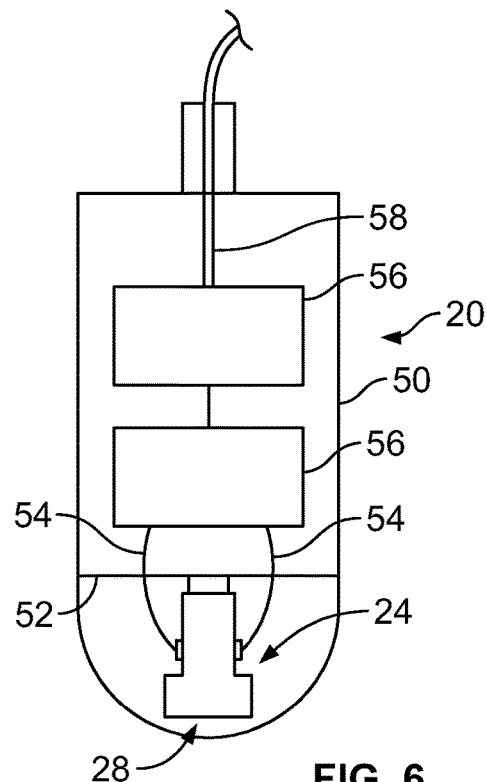
FIG. 6 is a schematic block diagram of an ultrasound probe in accordance with an embodiment.

FIG. 6 illustrates one embodiment of the ultrasound probe 20. It should be noted that the ultrasound probe 20 may take different configurations and may perform different types of imaging operations. The ultrasound probe 20 in the illustrated embodiment may be in communication with a host system and includes a housing 50 containing various components therein. The housing 50 may include one or more chambers or may be a single chamber.

As can be seen, the transducer array 28 on the MID 24 is mounted within the housing 50, such as to a support member 52. It should be noted that the support member 52 may be any structure configured to couple the MID 24 within the ultrasound probe 20. It should be appreciated that in some embodiments the MID 24 may be coupled directly to the housing 50.

The MID 24 allows for connection of the transducer array 28 to other components within the housing 50, such as one or processing or control boards 56. In some embodiments, the processing or control boards 56 may be embodied as the processing or control boards 44 shown in FIG. 5. In various embodiments, one or more cables 54 or other interconnect members may electrically connect the transducer array 28 via the electrical interconnects 32 of the MID 24 to the processing or control boards 56. Thus, the MID 24 may provide a transducer control arrangement for interconnecting the transducer array 28 to other components within the housing 50, such as from the scan head portion housing the MID 24. The cables 54 generally include one or more communication lines for communicating between the processing or control boards 56 and the transducer array 28, which may be connected to a system cable 58 for connection to a host system outside of the housing 50.

It should be noted that although the transducer driving arrangement and transducer control arrangement are described herein having specific component parts, these elements are not so limited. For example, the transducer driving arrangement may have a different shaft arrangement and the transducer control arrangement may have different control circuits or transmission lines. It also should be noted that additional or different component parts may be provided in connection with the probe 20 as needed or desired, and/or based upon the particular type and application of the probe 20. It further should be noted that the transducer array 28 may be configured for operation in different modes, such as, for example, a 1D, 1.25D, 1.5D, 1.75D, 2D, 3D and 4D modes of operation.

Figure 7:
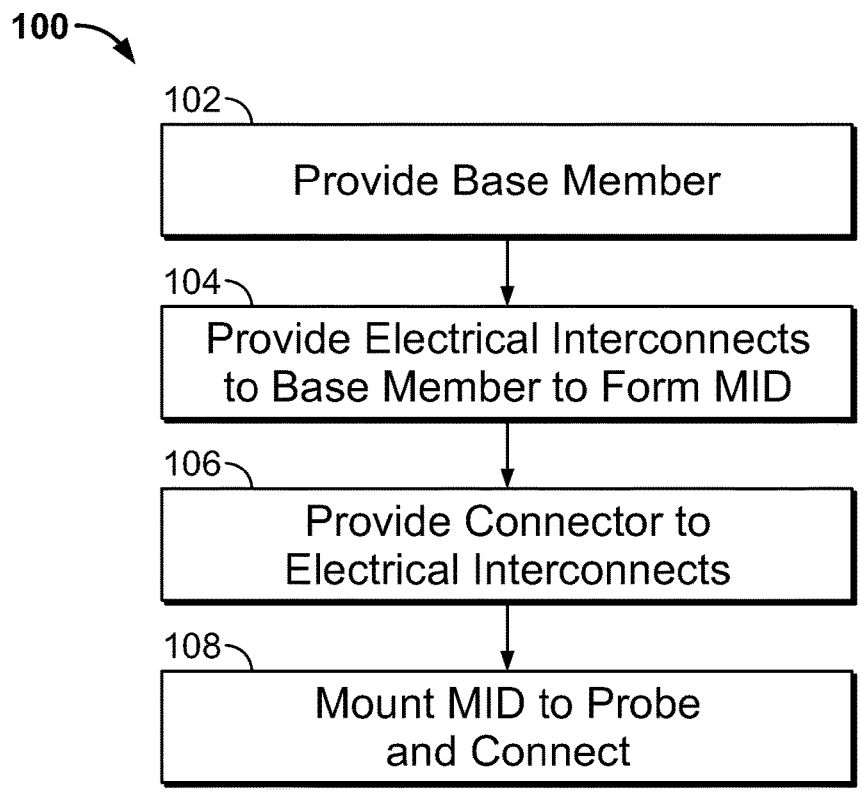
FIG. 7 is a flowchart of a method in accordance with various embodiments.

Various embodiments also provide a method 100 as shown in FIG. 7 for providing a connection arrangement for a transducer array in an ultrasound probe. The method 100, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the methods may be able to be used as one or more algorithms to direct hardware to perform operations described herein.

The method 100 includes providing a base member at 102. For example, a thermoplastic base material may be used to form a support structure for a transducer array. In some embodiments, the base material is a plastic material that may be injection molded using methods in the art to have a shape and size to support the transducer array. In various embodiments, the size and shape may be based on a desired configuration of the probe or desired operating characteristics of the probe or transducer array.

The method 100 includes providing electrical interconnects to the base member at 104 to form an integrated support and connection member, such as the MID 24. For example, the base may be etched or scribed, such as laser etched or scribed to form paths on the base and for deposition of metal thereon to form metal traces that are the electrical interconnects. For example, the laser etching in some embodiments is performed on a plastic base having a specialized metal complex in plastic that is activated or claimed by the laser etching. In some embodiments, a plating bath may be used to deposit metal (e.g., copper) to form the metal traces.

The method 100 also includes providing a connector to the electrical interconnects at 106. For example, an electrical interface or connector may be coupled to the MID to allow connection thereto of an external connection, such as a cable to connect to other components within the probe. The connectors may have a configuration (e.g., pin configuration) to allow connection to, for example, a particular cable. The method 100 further includes mounting the MID to the probe at 108 including connecting the MID therein. For example, when mounted within the probe, the MID provides the mechanical support for the transducer array to maintain the positioning of the transducer array, as well as to make electrical connection therein. Thus, the MID provides the merged or combined functionality of mechanical support and electrical connection.

It should be noted the various embodiments may provide an integrated support and electrical connection component for use in communicating any type of electrical signal and not only for particular ultrasound signals. For example, instead of providing signals for ultrasound operation, such as to control the transducer array and receive signals therefrom, the various embodiments may be used to provide signals for an indicator function, such as for a status indicator light of the probe. The various embodiments may also be used to integrate components within the housing of the probe or other portions of the probe in addition to or instead of the base.

Other embodiments may provide integrated components, such as for EMI shielding, connections for a button, integration of a thermistor, among others. For example, the integrated functionality may be part of different portions of the probe.

Figure 8:
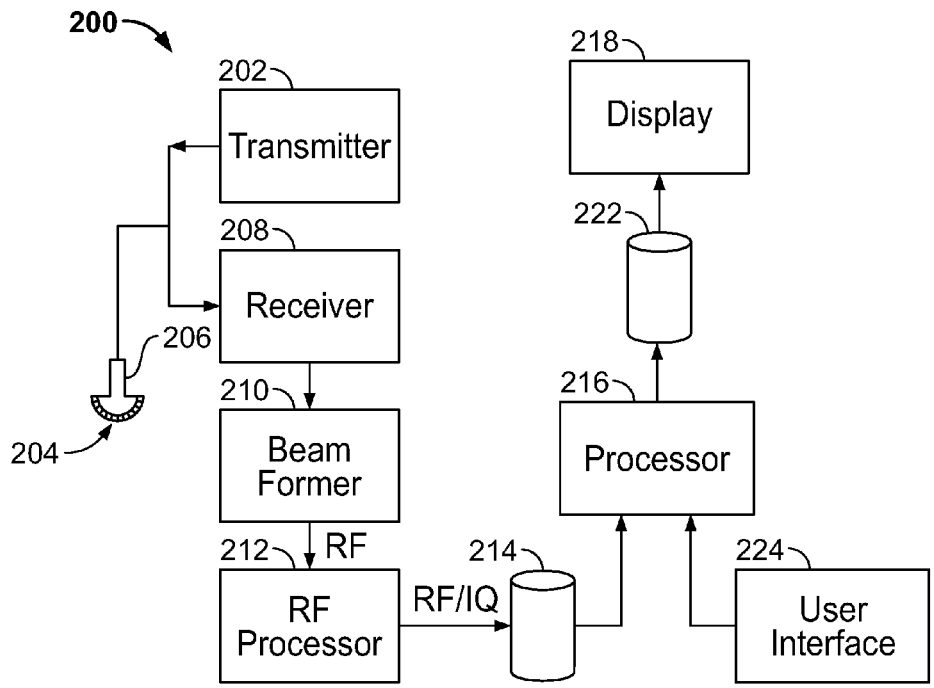
FIG. 8 is a block diagram of an ultrasound system in which various embodiments may be implemented.

The various embodiments described herein may be implemented in connection with an imaging system shown in FIG. 8. Specifically, FIG. 8 illustrates a block diagram of an exemplary ultrasound system 200 that is formed in accordance with various embodiments. The ultrasound system 200 includes a transmitter 202, which drives a plurality of transducers 204 within an ultrasound probe 206 (which may be embodied as the ultrasound probe 20 with the MID 24 in some embodiments) to emit pulsed ultrasonic signals into a body. A variety of geometries may be used. For example, the probe 206 may be used to acquire 2D, 3D, or 4D ultrasonic data, and may have further capabilities such as 3D beam steering. Other types of probes 206 may be used. The probe 206 also may be embodied as the probe 20 described herein having the connection member 36. The ultrasonic signals are back-scattered from structures in the body, like blood cells or muscular tissue, to produce echoes, which return to the transducers 204. The echoes are received by a receiver 208. The received echoes are passed through a beamformer 210, which performs beamforming and outputs an RF signal. The beamformer may also process 2D, 3D and 4D ultrasonic data. The RF signal then passes through an RF processor 212. Alternatively, the RF processor 212 may include a complex demodulator (not shown) that demodulates the RF signal to form IQ data pairs representative of the echo signals. The RF or IQ signal data may then be routed directly to RF/IQ buffer 214 for temporary storage.

The ultrasound system 200 also includes a signal processor 216. The signal processor 216 processes the acquired ultrasound information (i.e., RF signal data or IQ data pairs) and prepares frames of ultrasound information for display on a display 218. The signal processor 216 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 214 during a scanning session and processed in less than real-time in a live or off-line operation. A user interface, such as user interface 224, allows an operator to enter data, enter and change scanning parameters, access protocols, select image slices, and the like. The user interface 224 may be a rotating knob, switch, keyboard keys, mouse, touch screen, light pen, or any other suitable interface device.

The ultrasound system 200 may continuously acquire ultrasound information at a frame rate that exceeds 50 frames per second—the approximate perception rate of the human eye. The acquired ultrasound information, which may be the 3D volume dataset, is displayed on the display 218. The ultrasound information may be displayed as B-mode images, M-mode, volumes of data (3D), volumes of data over time (4D), or other desired representation. An image buffer (e.g., memory) 222 is included for storing processed frames of acquired ultrasound information that are not scheduled to be displayed immediately. The image buffer 222 in one embodiment is of sufficient capacity to store at least several seconds worth of frames of ultrasound information. The frames of ultrasound information are stored in a manner to facilitate retrieval thereof according to its order or time of acquisition. The image buffer 222 may comprise any known data storage medium.

Figure 9:
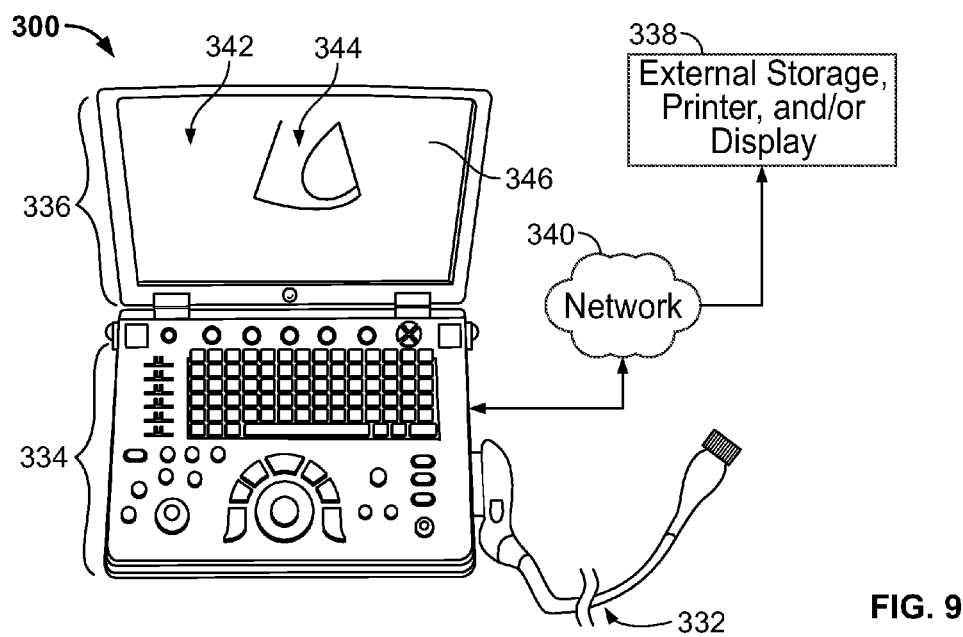
FIG. 9 is a diagram illustrating a miniaturized ultrasound system in which various embodiments may be implemented.
Figure 10:
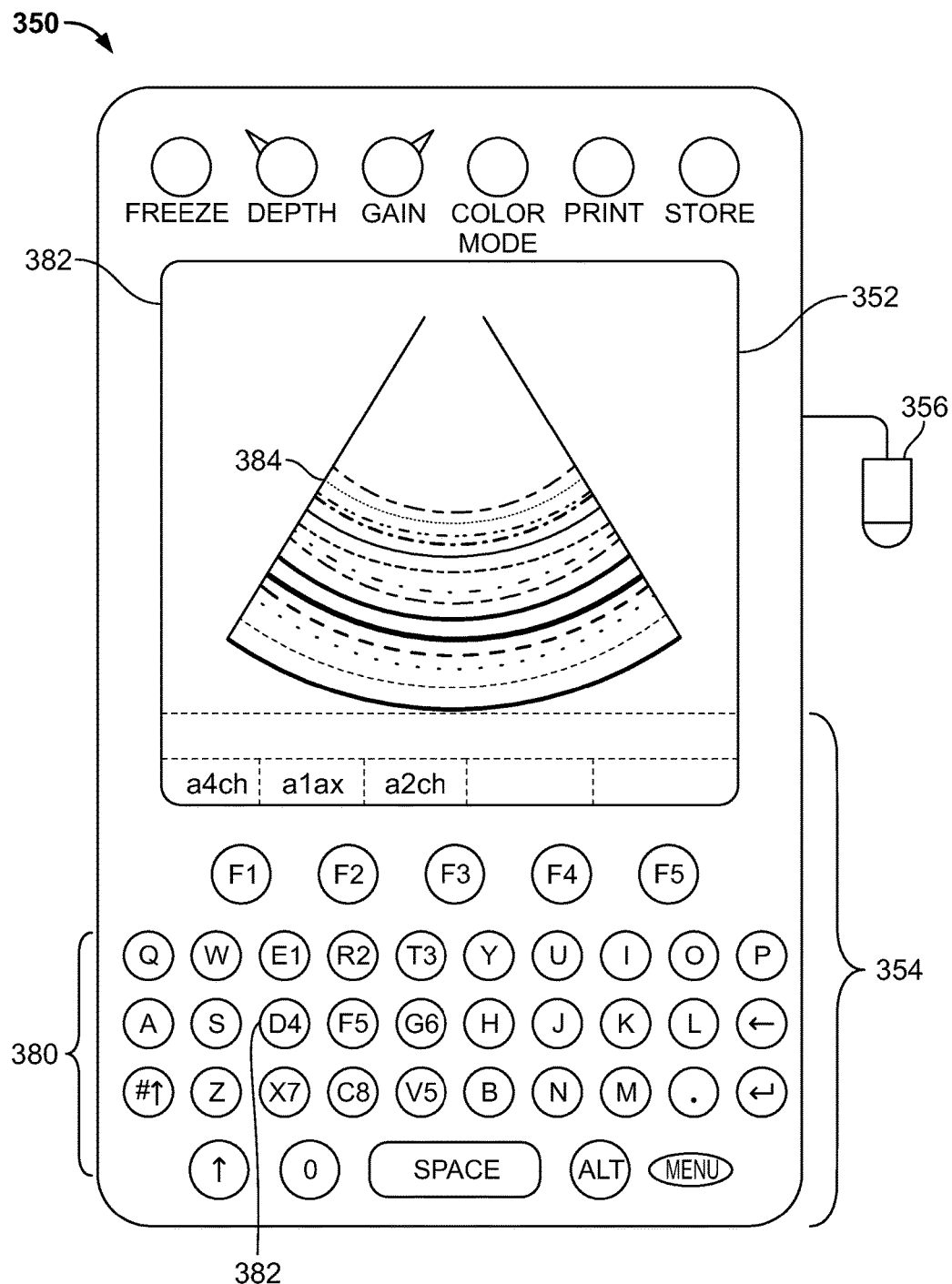
FIG. 10 is a diagram illustrating a hand carried or pocket-sized ultrasound imaging system in which various embodiments may be implemented.
Figure 11:
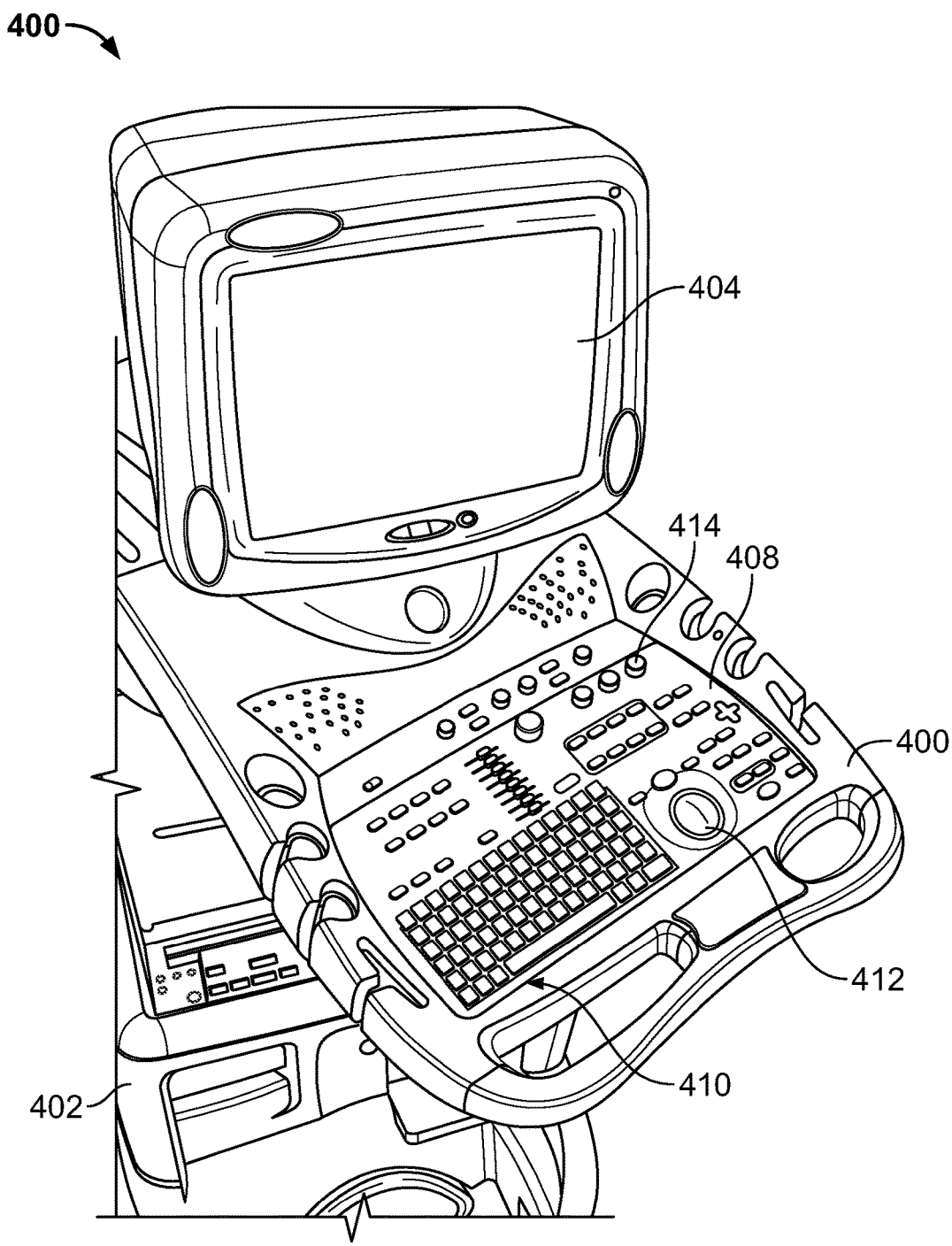
FIG. 11 is a diagram illustrating a console type ultrasound imaging system in which various embodiments may be implemented.

The ultrasound system 200 may be embodied in a small-sized system, such as, but not limited to, a laptop computer or pocket sized system as well as in a larger console-type system. FIGS. 9 and 10 illustrate small-sized systems, while FIG. 11 illustrates a larger system.

FIG. 9 illustrates a 3D-capable miniaturized ultrasound system 300 having an ultrasound transducer 332 that may be configured to acquire ultrasound data, such as 3D ultrasonic data or multi-plane ultrasonic data. For example, the ultrasound transducer 332 may have a 2D array of acoustic elements. A user interface 334 (that may also include an integrated display 336) is provided to receive commands from an operator. As used herein, "miniaturized" means that the ultrasound system is a handheld or hand-carried device or is configured to be carried in a person's hand, pocket, briefcase-sized case, or backpack. For example, the ultrasound system 300 may be a hand-carried device having a size of a typical laptop computer. The ultrasound system 300 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 300 and of displaying or printing images that may have greater resolution than the integrated display 336.

FIG. 10 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, and an ultrasound transducer 356. The display 352 may be, for example, a 320×320 pixel color LCD display (on which a medical image 384 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 382. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 382 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 300 and the miniaturized ultrasound system 350 may provide the same scanning and processing functionality as the system 200 (shown in FIG. 8).

FIG. 11 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and/or the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

It should be noted that although the various embodiments may be described in connection with an ultrasound system, the methods and systems are not limited to ultrasound imaging or a particular configuration thereof. The various embodiments of ultrasound imaging may be implemented in combination with different types of imaging systems, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and/or the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the teens "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A transducer support for an ultrasound probe, the transducer support comprising:
   a base configured to support thereon an ultrasound transducer array; and
   a plurality of electrical interconnects integrated with the base and configured to connect to the ultrasound transducer array, the plurality of electrical interconnects extending along at least a portion of the base from the ultrasound transducer array.

2. The transducer support of claim 1, wherein the base comprises a thermoplastic material and the plurality of electrical interconnects are laser etched metal traces within the thermoplastic material.

3. The transducer support of claim 1, further comprising a dematching layer forming a portion of the transducer array, wherein the dematching layer is electrically coupled to the plurality of electrical interconnects.

4. The transducer support of claim 1, further comprising at least one connector coupled to the base, wherein the connector is electrically coupled to at least some of the plurality of electrical interconnects.

5. The transducer support of claim 1, wherein the base and plurality of electrical interconnects form a molded interconnect device (MID).

6. The transducer support of claim 1, wherein the electrical interconnects comprise a plurality of electrically insulated metal traces.

7. The transducer support of claim 1, wherein the plurality of electrical interconnects extend along a top surface of the base and along at least one side surface of the base.

8. An ultrasound probe comprising:
   a housing;
   a scan head within the housing, the scan head including a transducer array supported on a molded interconnect device (MID), wherein the MID includes integrated electrical interconnects electrically connected to the transducer array; and
   at least one processing or control board within the housing, the processing or control board electrically connected to the transducer array via the electrical interconnects of the MID.

9. The ultrasound probe of claim 8, wherein the MID comprises a base formed from a thermoplastic material and the electrical interconnects are laser etched metal traces within the thermoplastic material.

10. The ultrasound probe of claim 8, further comprising a dematching layer forming a portion of the transducer array, wherein the dematching layer is electrically coupled to the electrical interconnects.

11. The ultrasound probe of claim 8, wherein the MID comprises a base and further comprising at least one connector coupled to the base, wherein the connector is electrically coupled to at least some of the electrical interconnects, the connector configured to couple to a cable interconnected with the processing or control board.

12. The ultrasound probe of claim 8, wherein the electrical interconnects comprise a plurality of electrically insulated metal traces.

13. The ultrasound probe of claim 8, wherein MID comprises a base and the electrical interconnects extend along a top surface of the base and along at least one side surface of the base.

14. The ultrasound probe of claim 8, wherein the MID comprises a base formed from an injection-molded thermoplastic material having a heat activated metal complex.

* * * * *